(12) United States Patent
Sheftel et al.

(10) Patent No.: US 9,707,172 B2
(45) Date of Patent: Jul. 18, 2017

(54) DEVICE AND METHOD FOR TREATING NEUROPATHY

(71) Applicants: Scott Sheftel, Tucson, AZ (US);
Stanley N. Sheftel, Akron, OH (US)

(72) Inventors: Scott Sheftel, Tucson, AZ (US);
Stanley N. Sheftel, Akron, OH (US)

( * ) Notice: Subject to any disclaimer, the term of this patent is extended or adjusted under 35 U.S.C. 154(b) by 140 days.

(21) Appl. No.: 14/864,541

(22) Filed: Sep. 24, 2015

(65) Prior Publication Data
US 2016/0008273 A1    Jan. 14, 2016

Related U.S. Application Data

(63) Continuation-in-part of application No. 14/213,735, filed on Mar. 14, 2014, now Pat. No. 9,192,761.

(60) Provisional application No. 61/785,674, filed on Mar. 14, 2013.

(51) Int. Cl.
| | |
|---|---|
| *A61K 9/00* | (2006.01) |
| *A61F 13/00* | (2006.01) |
| *A61N 1/32* | (2006.01) |
| *A61K 33/30* | (2006.01) |
| *A61N 1/20* | (2006.01) |

(52) U.S. Cl.
CPC ...... *A61K 9/0009* (2013.01); *A61F 13/00063* (2013.01); *A61K 9/0014* (2013.01); *A61K 9/0087* (2013.01); *A61K 33/30* (2013.01); *A61N 1/205* (2013.01); *A61N 1/32* (2013.01)

(58) Field of Classification Search
None
See application file for complete search history.

(56) References Cited

U.S. PATENT DOCUMENTS

| | | | | |
|---|---|---|---|---|
| 4,425,917 | A | 1/1984 | Kuznetz | 607/110 |
| 5,445,901 | A | 8/1995 | Korall et al. | 429/27 |
| 5,861,044 | A | 1/1999 | Crenshaw | 8/115 |
| 6,602,811 | B1 | 8/2003 | Rock et al. | 442/312 |
| 2002/0086036 | A1 | 7/2002 | Walker | 424/236.1 |
| 2005/0010192 | A1 | 1/2005 | Sun et al. | 604/501 |
| 2007/0191756 | A1 | 8/2007 | Tapper | 604/20 |
| 2010/0209515 | A1 | 8/2010 | Chantalat et al. | 424/490 |
| 2012/0016446 | A1 | 1/2012 | Panting | 607/62 |
| 2012/0064313 | A1 | 3/2012 | Rock et al. | 428/212 |

FOREIGN PATENT DOCUMENTS

| | | | |
|---|---|---|---|
| WO | WO2010027792 | 3/2010 | A61N 1/20 |

OTHER PUBLICATIONS

Anonymous, "Micro Current Technology," downloaded Feb. 10, 2015 from http://www.bio-therapeutic.in/micro-current-technology.php (5 pgs).

Anonymous, "Microcurrent Stimulation and Microcurrent Therapy," downloaded Feb. 10, 2015, from http://www.microcurrentsystems.com ) (5 pgs).
Anonymous, "Ohm's Law (again!)," Electrical Safety-Electronics Textbook, downloaded Mar. 8, 2015 from http://www.allaboutcircuits.com/vol_1/chpt-3/4.html (6 pgs).
Bogie et al., "Effects of regular use of neuromuscular electrical stimulation on tissue health," Journal of Rehabilitation Research and Development. vol. 40, No. 6, Nov./Dec. 2003, pp. 469-476 (7 pgs).
Bolton et al., "Direct-Current Bactericidal Effect on Intact Skin," Antimicrobial Agents and Chemotherapy, Jul. 1980, pp. 137-141 (5 pgs).
Carter et al., "Electric current flow through human skin at power frequency voltages," Brit. J. Industr. Med., 1969, 26, pp. 217-233 (7 pgs).
Chandak et al., "Modern Homeopathy An evidence based information on Homoeopathy," website: http://www.modernhomeopathy.com/anndt%20law.htm as of Oct. 8, 2015 (2 pgs).
Cheng et al., "The Effects of Electric Currents on ATP Generation, Protein Synthesis, and Membrane Transport in Rat Skin," Clinical Orthopaedics and Related Research, 171, (Nov.-Dec. 1982) pp. 264-272 (9 pgs).
Cole, K.S., "Electrical Conductance of Biological Systems," Cold Spring Harbor Symposia on Quantitative Biology, 1933, 1:107-116 (excerpt only) (1 pg).
Fish et al., *Medical and Bioengineering Aspects of Electrical Injuries*, Lawyers & Judges Publishing Company, 2003, book overview (13 pgs).
International Search Report issued in application No. PCT/US2014/029239, dated Sep. 24, 2015 (8 pgs).
International Search Report issued in application No. PCT/US2014/029239, dated Jul. 7, 2014 (12 pgs).
Kirsch et al., "Electromedicine: The Other Side of Physiology," Innovations in Pain Management: A Practical Guide for Clinicians (6th ed.) Boca Raton, Fla., 2002, American Academy of Pain Management, CRC Press, pp. 749-758 (14 pgs).
Ladizinsky, et al., "New Insights Into Oxygen Therapy for Wound Healing," Wounds, 2010, vol. 22, No. 12, pp. 294-300. (11 pgs).
Lambert et al., "Electro-membrane microcurrent therapy reduces signs and symptoms of muscle damage," Medicine & Science in Sports & Exercise, 2002, vol. 34, No. 4, pp. 602-607 (6 pgs).
McMakin, C., "Microcurrent therapy: a novel treatment method for chronic low back myofascial pain," Journal of Bodywork and Movement Therapies, 2004, 8, pp. 143-153 (11 pgs).
Miscellaneous, "Doctors' Comments," downloaded Oct. 8, 2015 from http://www.drionics.com (5 pgs).
Office Action issued in U.S. Appl. No. 14/213,735, dated Feb. 3, 2015 (10 pgs).
Office Action issued in U.S. Appl. No. 14/213,735, dated Jun. 19, 2015 (7 pgs).

(Continued)

*Primary Examiner* — Robert A Wax
*Assistant Examiner* — Randeep Singh
(74) *Attorney, Agent, or Firm* — Hayes Soloway P.C.

(57) ABSTRACT

Device and method for treating hyperhidrosis, neuropathy, skin, circulation, muscle stimulation, by application of a fabric including an elemental zinc particle deposition to a treatment area of the skin.

20 Claims, 4 Drawing Sheets

(56) References Cited

OTHER PUBLICATIONS

Office Action issued in U.S. Appl. No. 14/213,735, dated Oct. 7, 2014 (13 pgs).
Park et al., "The Effect of Microcurrent Electrical Stimulation on the Foot Blood Circulation and Pain of Diabetic Neuropathy," Journal of Physical Therapy Science, 2011, vol. 23, No. 3, pp. 515-518 (4 pgs).
Pfeiffer, E.A., "Electrical stimulation of sensory nerves with skin electrodes for research, diagnosis, communication and behavioral conditioning: a survey," Medical Biological Engineering, 1968, vol. 6, issue 6, pp. 637-651 (7 pgs).
Poltawski et al., Bioelectricity and microcurrent therapy for tissue healing—a narrative review, Physical Therapy Reviews, 2009, vol. 14, No. 2, pp. 105-114 (9 pgs).
Richter, C.P., "Physiological factors involved in the electrical resistance of the skin," American Journal of Physiology. vol. 88, 1929, pp. 596-615 (abstract only) (1 pg).
Rowlerson et al., "The fibre-type composition of the first branchial arch muscles in carnivore and primates," Journal of Muscle Research & Cell Motility Aug. 1983, vol. 4, issue 4, pp. 443-472 (5 pgs).
Suzuki, D., "The Body Electric," Skin Inc., Oct. 2007, downloaded from http://www.skininccom/skinscience/physiology/17969919.html (6 pgs).
Wang, W., "Oxygen partial pressure in outer layers of skin: simulation using three-dimensional multilayered models," Microcirculation, Mar. 2005, vol. 12, No. 2, pp. 195-207 (abstract only) (2 pgs).

DEVICE AND METHOD FOR TREATING NEUROPATHY

CROSS-REFERENCE TO RELATED APPLICATION

This application is a continuation-in-part of U.S. application Ser. No. 14/213,735, filed Mar. 14, 2014, which application in turn claims priority to a U.S. provisional Application filed on Mar. 14, 2013 and having Ser. No. 61/785,674.

BACKGROUND OF THE INVENTION

Embodiments generally relate to devices and methods for treatment of human and animal conditions. The invention has particular utility for treatment of conditions such as hyperhidrosis, and neuropathy as well as skin, circulation and muscle stimulation, and will be described in connection with such utilities, although other utilities are contemplated.

By way of example, hyperhidrosis is a medical condition in which patients experience excessive sweating. Patients suffering from hyperhidrosis may sweat even when they are resting or the temperature is cool. People naturally sweat when triggered by warm temperatures, exercise, nervousness, fear or anger. However, hyperhidrosis patients sweat excessively without these triggers and appear to have overactive sweat glands. Such uncontrolled sweating can lead to a patient's physical and emotional discomfort.

Current treatments, such as antiperspirants may mask odors from perspiration but fail to prevent sweat release from the skin surface. Other treatment methods including medication, iontophoresis, botulinum toxin injections, or surgery are invasive and may place some patients at risk.

In our aforesaid parent application, we describe a device for treating hyperhidrosis which comprises a fabric and zinc particles disposed on at least a portion of the fabric, wherein the fabric is configured to contact a body surface such that the zinc particle pattern comes in contact with a skin surface. We also describe a method for treating hyperhidrosis which comprises disposing onto a skin surface of a patient in need thereof a device including a fabric and a first metal disposed on the fabric. The fabric is configured to contact a body surface such that the zinc particle pattern comes in contact with a skin surface. In accordance with the present invention we have found that fabrics made in accordance with the teachings of our aforesaid parent application advantageously also may be used for treating a variety of other conditions suffered by both humans and animals, in addition to hyperhidrosis. Other conditions include for example, neuropathic pain including peripheral artery disease and neuropathy, surgical rehabilitation including joint surgery rehabilitation, surgery convalescence including joint surgery rehabilitation and soft tissue healing; physical therapy including muscle and tendon healing and stroke rehabilitation. Additionally, the present invention has been found to enhance athletic performance, endurance and faster recovery after exertion along with less muscle discomfort and fatigue.

The present invention also provides improved methods for manufacturing fabrics useful for treating various conditions as above described.

SUMMARY OF THE INVENTION

The present invention uses elemental zinc particles carried onto one surface of fabric as a plurality of dots or lines in a specific pattern that positions the zinc reservoirs in discrete locations, each location separated by a distance. This zinc-carrying fabric is placed with the zinc particles in contact with the skin of a person or animal and generates an electric current. More particularly, the zinc-carrying fabric configuration couples with oxygen and moisture at the skin surface to create a zinc-oxygen battery which produces an electric current at the skin.

The mechanism of action is the creation of a zinc-oxygen battery (13). The zinc-carrying fabric pattern acts as a half-cell anode and the oxygen at the skin surface acts as a half-cell cathode. The human or animal's body contributes moisture, which completes the circuit. The completed circuit creates a redox reaction with oxidation of the zinc and reduction of the oxygen ($2Zn+O_2 \rightarrow 2ZnO$). The oxygen is ambient or replenished with the circulating blood oxygen (partial pressure of oxygen diffusing through the skin) at the skin's surface (22,23).

Microcurrent stimulation is a known phenomena in the range of millionths of an ampere. Humans and other animals have inherent electrical (microcurrent) properties that drive and maintain their bodies. Cells communicate with one another via complex neuro pathways generated and maintained by biochemical reactions that create electrical activity. The body generates electrical fields in vital organs such as the heart and brain that are easily measured with instruments such as EEG (electroencephalogram), and EKG (electrocardiogram). Studies of microcurrent stimulation have been well documented for decades. The effect on the human body is evident both clinically and on a cellular level (11,14,16). Physiologic studies document increased capillary density, enhanced blood flow and tissue oxygenation, as well as an enhanced cellular response with increased protein synthesis, amino acid transport and increased ATP (mitochondrial energy) synthesis (3,4,11,15,16,19). In addition to amplifying critical cellular functions within the cell, microcurrent also may increase local cellular absorption of nutrients and facilitates waste elimination, a critical component of muscle performance and recovery (3,11,12,15,17).

While low doses of electricity stimulate cellular activity, higher doses can suppress or inhibit cellular function (7,8). An example of inhibitory activity is seen with the effect of electrical current on sweat production and bacterial growth (1). The efficacy of applying external electrical current to the skin for control of excessive sweating (hyperhidrosis) is historically well documented (20,21). This concept is the basis for hyperhidrosis treatments utilizing external battery devices such as marketed under the name Drionics, available from General Medical Company. In addition to reducing sweat gland activity, electrical current inhibits the activity of bacteria and fungi, the organisms responsible for foot odor and athletes foot (7,21).

The present invention in one aspect provides a self-contained fabric device which creates a zinc-oxygen battery at the skin's surface with microcurrent stimulation under the fabric surface. The current delivered is of the magnitude of micro-amps (microcurrent). In our patent application, we describe the effect on the sweat glands with reduced sweating. The current continuation-in-part we explain the mechanism of action, provide expanded benefits and uses, and provide improved methods for forming the fabric device.

Historically microcurrent stimulation is not a new concept. It is well documented that microcurrent stimulates skin, sweat glands and underlying muscle. What is new and unique about our device is that the zinc-fabric device forms a first half cell of a battery circuit. The body forms a second half cell of the battery circuit with the ready supply of oxygen both ambient and diffused through the skin surface (22,23). The moisture from the skin completes the circuit resulting in creation of a zinc-oxygen battery.

We have used our zinc coated fabric in medical and athletic clothing applications. Athletic participants have reported that the microcurrent stimulation enhances athletic performance, endurance and faster recovery after exertion along with less muscle discomfort and fatigue. Medical participants have reported that the microcurrent stimulation helped with nerve, muscle and joint discomfort with activities.

The present invention, in another aspect provides methods for manufacturing zinc-coated fabrics in accordance with the present invention. These methods include but are not limited to silk screen printing, ink jet printing, 3-D printing; fusion printing; stencil printing, Xerography printing, ink drop printing and other such methods capable of transferring a binder and zinc particles, in a pattern to a textile surface.

BRIEF DESCRIPTION OF THE DRAWINGS

The invention will be better understood from a reading of the following detailed description taken in conjunction with the drawings in which like reference designators are used to designate like elements, and in which.

DETAIL DESCRIPTION OF THE PREFERRED EMBODIMENTS

The invention is described in preferred embodiments in the following description with reference to the drawing figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," "in certain embodiments," and similar language throughout this specification may, but do not necessarily, all refer to the same embodiment. It is noted that, as used in this description, the singular forms "a," "an" and "the" include plural referents unless the context clearly dictates otherwise.

The described features, structures, or characteristics of the invention(s) may be combined in any suitable manner in one or more embodiments. In the following description, numerous specific details are recited to provide a thorough understanding of embodiments of the invention(s). One skilled in the relevant art will recognize, however, that the invention(s) may be practiced without one or more of the specific details, or with other methods, components, materials, and so forth. In other instances, well-known structures, materials, or operations are not shown or described in detail to avoid obscuring aspects of the invention.

Figure 1:
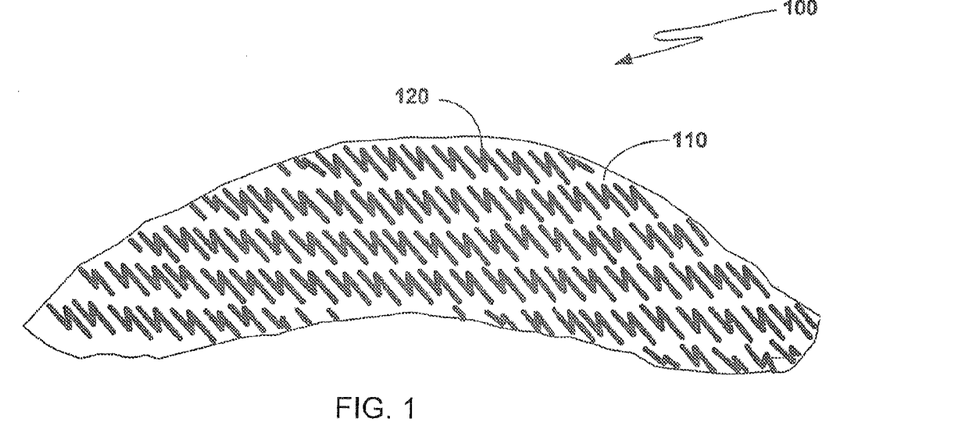
FIG. 1 illustrates an exemplary embodiment of Applicants' device for treatment of hyperhidrosis in the form an underbra insert including a pattern of metal deposition. As illustrated, this embodiment includes many discontinuous areas of metal deposition in which the overall fabric surface area is greater than the overall surface area of individual patterns of metal deposition.
Figure 2A:
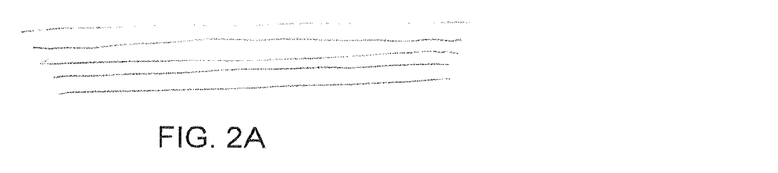
FIGS. 2A-2E illustrate various patterns of metal deposition on fabric in accordance with the present invention. These are also the patterns used with the athletic clothing stimulating the skin, circulation and underlying muscles.
Figure 2B:
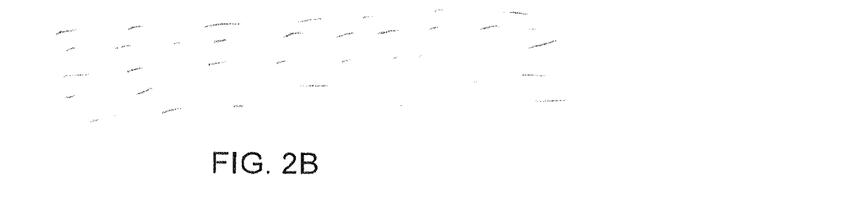
Figure 2C:
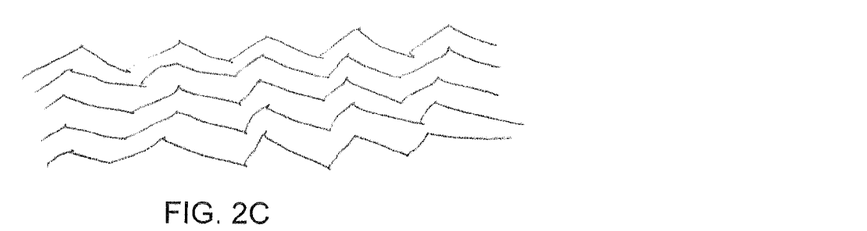
Figure 2D:
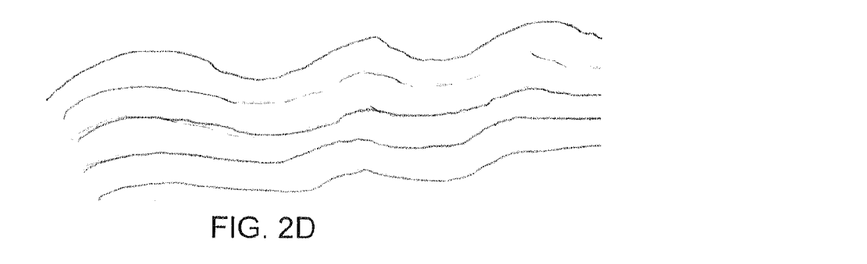
Figure 2E:
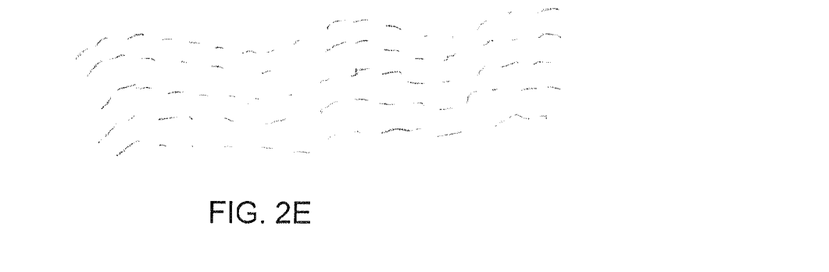

Referring to FIG. 1, an embodiment of Applicants' device for treating hyperhidrosis is illustrated. As shown, Applicants' device comprises an underbra insert 100 that includes a fabric 110 and a plurality of metal deposition areas 120. As shown, the plurality of individual metal deposition areas 120 are discontinuous and uniformly distributed on the surface of the fabric 110, in imaginary spaced lines or lines of dots, to cover a substantially consistent percentage of the surface area of the fabric 110. Typically, the lines or lines of dots are evenly spaced at spacings from 0.1 to 3 mm, preferably 0.2 to 2 mm, more preferably 0.3 to 1.5 mm, most preferably 0.5 to 1.0 mm. The concentration of zinc in the binder that forms the line or deposition determines the amount of zinc available for the battery. Preferred concentration is 30% but the lowest is about 1% and the highest about 50%. The mixture of binder and metal forms a paste that can be applied by silk screening wherein the paste viscosity is important. A 30% by weight zinc to binder is preferred for this. The line width and length also determines the amount of zinc in the deposition since the wider and longer the line, the more zinc is available. Preferred line or line of dots width is 1 mm width but width can vary from 0.1 mm up to 5 mm width. Since the deposition is on a fabric, the amount of binder/zinc applied can also be varied. In certain embodiments, the article being coated can be coated twice or more times over the same spot wherein the thickness of the deposition can be increased as desired. In certain embodiments, the metal deposition area patterns 120 cover from about 10% to about 90% of the surface area of the fabric. In other embodiments, the metal deposition areas 120 cover from about 20% to about 80%, from about 15% to about 75%, from about 25% to about 50%, or from about 30% to about 40% of the surface area of the fabric 110. Although FIG. 1 shows the plurality of metal deposition areas 120 substantially uniformly distributed on the surface of the fabric 110, in other embodiments, the plurality of metal deposition areas 120 may be randomly distributed on the surface of the fabric 110. Typically, the lines have a thickness of 0.1 to 3 mm, preferably 0.2 to 2 mm, more preferably 0.3 to 1.0, most preferably 0.4 to 0.5 mm. The spaced lines may be continuous and may take various forms including straight, curved and various angular shapes as shown, for example, straight continuous lines are shown in FIG. 2A; straight broken lines are shown in FIG. 2B; continuous saw-shaped as shown in FIG. 2C; continuous wavy lines as shown in FIG. 2D; broken wavy lines as shown in FIG. 2E, etc. The actual shape of the lines is not important. Preferably, but not necessarily, the lines are approximately equal in thickness and are evenly spaced.

The underbra insert fabric 110, as illustrated in the embodiment of FIG. 1, comprises a single layer. However, in other embodiments, the fabric 110 may comprise one, two, or three or more layers of fabric including metal deposition areas on at least one surface of the device. The underbra insert 100 is worn inside a bra cup underneath the breast in contact with the skin as a bra underliner to treat excessive sweating associated with hyperhidrosis.

Preferably, but not necessarily, the fabric 110 comprises a woven textile, a non-woven textile, a fibrous mesh, a non-fibrous mesh, a textile mesh, or the like. In one embodiment, the fabric may comprise a polymeric film or a polymeric coating. In an embodiment, the fabric may be interwoven with elastic fibers, elastic bands, or metallic fibers. In certain embodiments, the fabric is electrically conductive or electrically non-conductive.

In certain embodiments, fabric 110 is permeable to ambient air. In certain embodiments, the plurality of individual metal deposition areas 120 comprise elemental zinc particles.

In an embodiment, the device includes a fastener configured to attach the device or the underbra insert 100 to the skin surface or to the surface of an article of clothing. For example, referring back to FIG. 1, in certain embodiments the surface of the fabric 110 comprises a surface of the fabric 110 including the plurality of metal deposition areas 120 in contact with the skin and an opposing surface of the fabric 110 in contact with an article of clothing. In certain embodiments, the opposing surface of the fabric 110 includes an adhesive configured to attach the fabric 110 to an article of clothing. For example, the underbra insert 100 as shown in FIG. 1 includes the plurality of metal deposition areas 120 on one surface of the fabric 110 configured for contact with the skin surface. An opposite surface of the underbra insert 100 (not shown) includes an adhesive or adhesive strips configured to adhere the underbra insert 100 to the interior of a bra surface. In an embodiment, the device is configured for attachment to an article of clothing via at least one of the group consisting of a VELCRO® fastener, buttons, zippers, electrostatics, an adhesive, a hook and eye fastener, a thread, snaps, or the like.

In an embodiment, the surface of the fabric 110 including the plurality of metal deposition areas 120 further comprises an adhesive for attachment of the fabric to the skin surface. In an embodiment, the fabric of the device is flexible and/or conformable to the skin surface. In certain embodiments, the fabric of the device is compressive to the skin surface, for example and without limitation, a sock, a glove, a headband, or an elastic bandage.

In an embodiment, the fabric of the device comprises an article of clothing. For example, the fabric includes at least one member selected from the group consisting of a sock, a glove, a headband, a cap, a hat, a t-shirt, a bra, an underarm insert, pants, sleeves, underwear (undergarment clothing in contact with the skin), or compression clothing such as ankle, arm or knee sleeves, shorts and shirts. For example, FIGS. 3A and 3B illustrate exemplary embodiments of Applicants' device for treatment of diabetic neuropathy in the form of socks including a plurality of continuous lines of metal deposition.

Figure 3A:
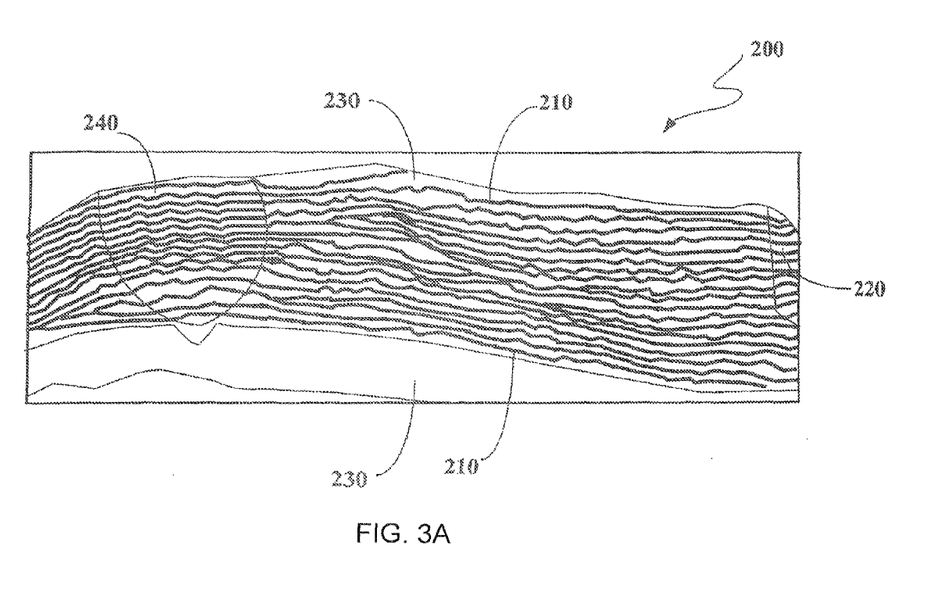
FIGS. 3A and 3B illustrate exemplary embodiments of Applicants' device for treatment of diabetic neuropathy in the form of socks, each sock including a plurality of continuous lines of metal deposition.
Figure 3B:
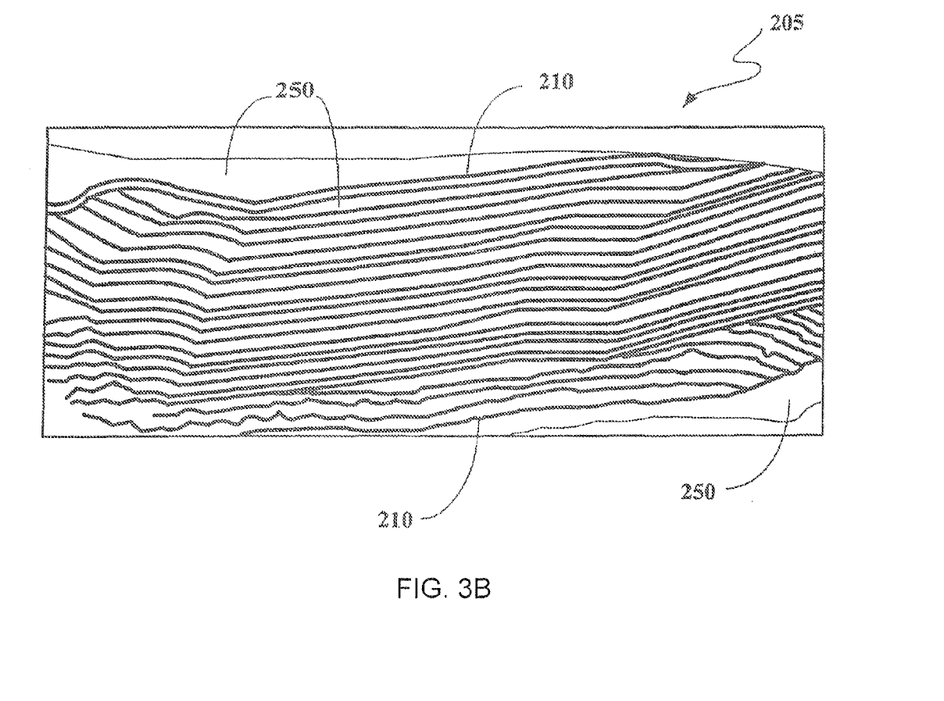

FIG. 3A illustrates sock 200 including a plurality of continuous lines of metal deposition 210, preferably evenly spaced from one another, a reinforced fabric 220 of a toe region, a fabric 230 of a body of the sock 200, and a reinforced fabric 240 of a conforming heel of the sock 200. Similarly, FIG. 3B illustrates sock 205 also including a plurality of continuous lines of metal deposition 210, and a fabric 250 of the sock 205 body. As shown in FIG. 3B, the sock 205 comprises a heelless sock including a conforming single sock body void of reinforced toe and heel regions. The materials comprising fabrics 220, 230, 240, and 250 and the plurality of continuous lines of metal deposition 210 comprise any of the materials discussed herein regarding the fabric 110 and the plurality of metal deposition areas 120 of exemplary device underbra insert 100. FIGS. 3A and 3B illustrate the width of each line of the plurality of continuous lines of metal deposition 210 is less than the width of fabric 250 between each line of the plurality of continuous lines of metal deposition 210. However, in certain embodiments the width of each line of the plurality of continuous lines of metal deposition substantially equals the width of fabric between each line of the plurality of continuous lines of metal deposition. By "substantially equals," Applicants mean within ± about 10% of the value of interest. In an embodiment, the width of each line of the plurality of continuous lines of metal deposition is greater than the width of fabric between each line of the plurality of continuous lines of metal deposition. In certain embodiments, the fabric 250 includes a ridged surface.

In certain embodiments, zinc is utilized as a powdered elemental crystal. In certain embodiments, the zinc utilized has a purity of about 99.99 percent however, zinc is available in other purities and particle sizes as defined by the user. In certain embodiments, the zinc comprises a −325 mesh size. As those skilled in the art will appreciate, particles passing through a −325 mesh are considered the "fines."

In certain embodiments, the zinc particles are very uniform in size. In certain embodiments, the zinc particle size distribution is between about 4 microns to about 10 microns in diameter. These individual particle crystals approach the visible range and are easily seen as shiny crystals on the surface.

In certain embodiments, Applicants' socks comprise a woven fabric. In certain embodiments, Applicants' socks comprise a non-woven fabric. In certain embodiments, Applicants' socks comprise a braided fabric. In certain embodiments, Applicants' socks comprise a polymeric fabric. In certain embodiments, Applicants' socks are permeable to ambient oxygen.

In certain embodiments, Applicant applies a zinc coating to the skin surface of a body part, such as and without limitation, a foot using an immersion printing technique. Such a process is sometimes referred to as water transfer printing, water transfer imaging, or cubic printing.

In the process, a polyvinyl alcohol film is coated with a coating of zinc particles and is then floated on the surface of a vat of water. An activator chemical is sprayed on the film to dissolve it into a liquid and activate a bonding agent. A patient's foot is then lowered into the vat, through the floating zinc layer, which wraps around and adheres to it.

In certain embodiments, zinc particles are disposed on a skin surface using a light tattoo.

In certain embodiments, Applicant utilizes a screen print method. A PVC silk screen ink is used as both as the vehicle and binder. Zinc particles are mixed into the ink and process it through the silk screens. The ink is heat cured under an oven to "set" the ink or make it solid. Since the zinc is a metal, this process does not affect the zinc, however, the ink is selected so to not encapsulate the zinc particles but leave them anchored to the fibers of the sock and exposed to the skin.

In certain embodiments, a plastisol ink is utilized in the screen printing process. Plastisol is a suspension of PVC particles in a liquid plasticizer. The suspension flows as a liquid. Zinc particles are mixed into the plastisol suspension, and that mixture is screen printed onto a fabric, such as and without limitation, a sock. In certain embodiments, the zinc/plastisol suspension is mixed with 20% Union stretch ink prior to application to the fabric.

When the coated fabric is heated to around 177 degrees Celsius, the plastic and plasticizer mutually dissolve each other. On cooling the mold below 60 degrees C., a flexible, permanently plasticized zinc coating is disposed onto the fabric.

In yet other embodiments of the invention, the zinc particles may be printed on the fabric using a stencil/fusion technique, by 3-D printing, ink drop printing or Xerography.

The present invention is unique in that the zinc pattern grid creates a matrix of individual half-cells (anodes) for ion exchange with the skin. One-half cell of electrochemical reaction is the zinc impregnated fabric (the anode), and the other is the skin of the human or animal, supplying moisture and oxygen (the cathode) completing the circuit for microcurrent production. Alternatively, the oxygen may be supplied, in part, from ambient air.

The chemistry of Zinc-air batteries is instructive. Such batteries are powered by oxidizing zinc with oxygen from the air. During discharge, zinc particles form a porous anode, which is saturated with an electrolyte, namely sweat. Oxygen from the air reacts at the cathode and forms hydroxyl ions which migrate into the zinc paste and form zincate $Zn(OH)_2$, releasing electrons to travel to the cathode.

The chemical equations for the zinc-air battery formed using Applicants' zinc-coated socks and ambient oxygen include:

$$\text{Anode: } Zn+4OH^- \rightarrow Zn(OH)_4^{2-}+2e^- (E_0=-1.25\text{ V})$$

$$\text{Fluid: } Zn(OH)_4^{2-} \rightarrow ZnO+H_2O+2OH^-$$

$$\text{Cathode: } \tfrac{1}{2}O_2+H_2O+2e^- \rightarrow 2OH^- (E_0=0.34\text{ V})$$

Overall, the zinc oxygen redox chemistry recited immediately hereinabove comprises an overall standard electrode potential of about 1.59 Volts.

There is a certain amount of gas exchange at the skin surface with a partial pressure of oxygen. The oxygen at the skin surface is a product of ambient oxygen in addition to oxygen diffusion from capillary blood flow. In certain embodiments, the zinc in contact with a patient's skin resulting from wearing, for example, my zinc-containing socks, in combination with sweat and transcutaneous oxygen complete the galvanic circuit described hereinabove.

The chemistry utilized by Applicants' zinc-coated socks differs from a more conventional galvanic cell. A galvanic cell, or voltaic cell is an electrochemical cell that derives electrical energy from spontaneous redox reactions taking place within the cell. It generally consists of two different metals connected by a salt bridge, or individual half-cells separated by a porous membrane. In contrast, the chemistry of Applicants' zinc-air battery does not require use of a second metal. Applicants' method to treat hyperhidrosis utilizes elemental zinc particles disposed onto a fabric, where the elemental zinc particles are in contact with the skin. In certain embodiments, other than elemental zinc metal and zinc oxides formed therefrom, no other or additional metals or metal oxides are needed or are utilized in Applicants' method and device.

In certain embodiments, a method for treating hyperhidrosis includes disposing onto a skin surface a device including a fabric having elemental zinc particles disposed thereon. The fabric is configured to contact the skin and to generate an electric current and metal ions when oxidized by ambient oxygen. The generation of such an electric current results in reducing the amount of sweat disposed on the skin surface thereby providing a treatment for hyperhidrosis.

In certain embodiments, Applicants' method for treating hyperhidrosis includes generating an electric current on the skin surface resulting in a reduction of an amount of sweat released by the skin. For example, in a non-limiting embodiment, the method includes contacting a skin surface with elemental zinc particles disposed on at least a portion of the fabric or flexible substrate.

The method described herein may include any of the fabric and metal materials previously described with respect to the exemplary device described herein (i.e., the underbra insert 100 or socks 200 and 205).

The following Example is presented to further illustrate to persons skilled in the art how to make and use the invention. This Example is not intended as a limitation, however, upon the scope of the invention, which is defined by claims recited hereinbelow.

EXAMPLE I

During the initial interview, study participants received protocol instructions and rated their neuropathy severity utilizing a standardized diabetic Neuropathy Total Symptom Score—6 (NTSS-6) questionnaire.

Participants were provided with 4 pairs of socks with only the right foot (clearly marked) treated with the zinc ions. They were asked to wear them as much as possible over a 21 day period and keep a wear record on a time grid. At the point they noticed an improvement in feeling of the right foot, they were asked to mark the time grid in red.

Participants reported wearing the socks from (8)14 to 24 hours each day. A decrease in neuropathy was noted in all participants, irrespective of gender and age, and persisted throughout the study period. Average time to note a relief of neuropathy symptoms was 9 days—the earliest noted on day 5 and the latest on day 13.

Preliminary results indicate that frequent exposure a diabetic's feet to the low current created by the zinc-containing socks resulted in a significant decrease in neuropathy that persisted once relief of symptoms became apparent to the participant.

Exit survey indicated that patients found the right sock to be comfortable and the right foot to have less neuropathy. They would like to have pairs with both socks treated, and would like to try other zinc-containing Sportswear clothing. They would recommend the zinc-containing socks to others and would purchase them if available.

While the preferred embodiments of the present invention have been illustrated in detail in connection with treatment of hyperhidrosis and diabetic neuropathy, various modifications and adaptations to those embodiments as possible without departing from the scope of the present invention as set forth herein.

For example, the invention also may be used to treat neuropathic pain including peripheral artery pain or other forms of neuropathy, surgery convalescence including joint and tissue rehabilitation, and physical therapy including muscle and tendon healing and stroke rehabilitation. Patients convalescing from joint surgery, wearing, the zinc coated fabric over the surgery site, reported less pain, increased endurance and subjectively faster recovery. Additionally, the present invention has been found to enhance athletic performance, endurance and faster recovery after exertion along with less muscle discomfort and fatigue. The applicants supplied a tennis team and college basketball team with the zinc embodied clothing. Their evaluations and reports complimented the applicant's observations with subjective evaluations of enhanced endurance and faster recovery after exertion along with less muscle discomfort and fatigue. Of note, the device may take the form of a temporary tattoo which is applied directly to the skin of the human or animal patient.

1. Bolton, L., B. Foleno, B. Means, and S. Petrucelli. (1980). Direct-Current Bactericidal Effect on Intact Skin. Antimicrobial Agents and Chemotherapy, July 1980, p. 137-141
2. Fish, R., and L. Geddes, *Medical and Bioengineering Aspects of Electrical Injuries*. C2003 lawyers and Judges Publishing Company, Inc.

3. Cheng, N., et al., The Effects of Electric Currents on ATP Generation, Protein Synthesis, and Membrane Transport in Rat Skin, Clinical Orthopaedics and Related Research, 171 264-272, (November-December 1982)
4. http://www.skininccom/skinscience/physiology/1796991.html
5. Richter, C. P. Physiological Factors Involved with the Electrical Resistance of the Skin. American Journal of Physiology. Vol. 88, 1929, 596-615.
6. http://www.allabout circuits.com/vol 1/chpt-3/4.html
7. http://www.modernhomeopathy.com/anndt%20law.htm
8. Cole, K. S., (1933) Electrical Conductance of Biological Systems. Sym. Quant. Biol. 1, 107-116
9. Carter, A. O. and R. Morley. (1969). Electric Current Flow Through Human Skin at Power Frequency Voltages. Brit. J. Industr. Med., 26, 217-233
10. Pfeiffer, Erich A. (1968). Electrical Stimulation of Sensory Nerves with Skin Electrodes for Research, Diagnosis, Communication and Behavioral Conditioning: A Survey. Medical and Biological Engineering, Volume 6, issue 6, 637-651.
11. Bogie, Kath M. DPhil, Ronald J. Triolo, PhD. (2003). Effects of Regular Use of Neuromuscular Electrical Stimulation on Tissue Health. Journal of Rehabilitation Research and Development. Vol. 40, No. 6, November/December 2003. 469-476.
12. Rowlerson (1983), The Fibre Type Composition of the First Branchial Arch Muscles in Carnivore and Primates. J. Muscles res Cell Motil 4, 443-472
13. Korall et al. Zinc-Oxygen Battery. U.S. Pat. No. 5,445,901.
14. Poltawski, L and Watson, T. (2009) Bioelectricity and Microcurrent Therapy for Tissue Healing_a Narrative Review, Physical Therapy Reviews 2009 Vol 14, No. 2. 105-114.
15. Kirsch, Daniel L. PhD. Electromedicine: The Other Side of Physiology, (2002) Pain Management: A Practical Guide for Clinicians (6th ed.) Boca Raton, Fla.: American Academy of Pain Management. Richard Weiner, Editor. CRC Press. 749-758.
16. Park, R J, H. Son, K. Kim, et al. (2011) The Effect of Microcurrent Electrical Stimulation on the Foot Blood Circulation and Pain of Diabetic Neuropathy. Journal of Physical Therapy Science (23)3: 515-518
17. Lambert, M I, Marcus P., Burgess T, Noakes T D. (2002). Electro-membrane Microcurrent
Therapy Reduces Signs and Symptoms of Muscle Damage. Med Sci Sports Exerc. April; 34 (4): 602-607.
18. McMakin, Carolyn R, M A, D C. Microcurrent Therapy: a Novel Treatment Method for Chronic Low Back Myofascial Pain. (2004). Journal of Bodywork and Movement Therapies. April (8)2:143-153.
19. http://www.microcurrentsystems.com
20. http://www.bio-therapeutic.in/micro-current-tehnology.php
21. http://www.drionics.com
22. Wang, W., Oxygen Partial Pressure in Outer Layers of Skin Simulation using Three-Dimensional Multilayered Models. (2005). Microcirculation. March; 12(2):195-207.
23. Ladizinsky, Daniel M D, Roe, David PhD. New Insights into Oxygen Therapy for Wound Healing. (2010), Wounds. 22(12):294-300.

We claim:

1. A device for relieving pain or promoting rehabilitation of an animal or human in need of same, or for enhancing athletic performance, comprising:
   a fabric or substrate;
   elemental zinc particles disposed on at least a portion of a surface of the fabric or substrate, as a plurality of lines or dots in a specific pattern that positions the zinc particles in discrete electrically isolated locations separated by a distance, wherein the fabric or substrate is configured such that said elemental zinc particles contact a skin surface of the human or animal, wherein the plurality of spaced lines are substantially evenly spaced from one other,
   wherein said fabric or substrate forms a plurality of half-cells of an air-zinc battery, for ion exchange with the skin of the human or animal.

2. The device of claim 1, wherein the patterns conform to blood circulation patterns and/or nerve or underlying muscle patterns of the human or animal.

3. The device of claim 1, wherein the lines or dots are evenly spaced at spacings from 0.1 to 3 mm, preferably 0.2 to 2 mm, more preferably 0.3 to 1.5 mm, most preferably 0.5 to 1 mm.

4. The device of claim 1, wherein the lines or dots of lines are 0.1 mm to 5 mm wide, preferably about 0.1 to 3 mm, more preferably 0.2 to 2 mm, even more preferably 0.3 to 1 mm, most preferably 0.4 to 0.5 mm.

5. The device of claim 1, wherein the patterns cover from about 10% to 90% of the surface of the fabric or substrate, preferably from about 15% to about 75%, more preferable from about 25% to about 50%, most preferably from about 30% to about 40%.

6. The device of claim 1, wherein the fabric or substrate comprises a fabric or substrate conformable to the skin surface.

7. The device of claim 1, wherein the fabric or substrate comprises a polymeric film.

8. The device of claim 1, wherein the fabric or substrate comprises a ridged surface.

9. The device of claim 1, wherein the fabric comprises an article of clothing.

10. The device of claim 1, wherein the fabric comprises at least one member selected from the group consisting of a sock, leggings, a glove, a headband, a cap, a hat, a t-shirt, and an underarm insert.

11. A method for relieving neuropathy, promoting tissue rehabilitation, muscle or tendon healing in a human or animal in need of same, or for enhancing athletic performance, comprising disposing onto a skin surface of the human or animal in need of same, a device comprising:
   a fabric or substrate;
   elemental zinc particles disposed on at least a portion of a surface of the fabric or substrate, as a plurality of lines or dots in a specific pattern that positions the zinc particles in discrete electrically isolated locations separated by a distance, wherein the fabric or substrate is configured such that said elemental zinc particles contact a skin surface of the human or animal, wherein the plurality of spaced lines are substantially evenly spaced from one other,
   wherein said fabric or substrate forms a plurality of half-cells of an air-zinc battery, for ion exchange with the skin of the human or animal.

12. The method of claim 11, wherein the pain comprises diabetic neuropathy.

13. The method of claim 11, wherein the fabric or substrate comprises a fabric or substrate conformable to the skin surface.

14. The method of claim 11, wherein the fabric or substrate comprises a polymeric film.

15. The method of claim 11, wherein the fabric or substrate comprises a ridged surface.

16. The method of claim 11, wherein the fabric or substrate comprises an article of clothing.

17. The method of claim 11, wherein the fabric or substrate comprises at least one member selected from the group consisting of a sock, leggings, a glove, a headband, a cap, a hat, a t-shirt and an underarm insert, and compression clothing selected from the group consisting of an ankle sleeve, an arm sleeve, a knee sleeve, compression shorts and a compression shirt.

18. A method for creating microcurrent stimulation of the skin of a human or animal, comprising disposing in contact with the skin of a human or animal, a fabric device comprising:
- a fabric or substrate;
- elemental zinc particles disposed on at least a portion of a surface of the fabric or substrate, as a plurality of lines or dots in a specific pattern that positions the zinc particles in discrete electrically isolated locations separated by a distance, wherein the fabric or substrate is configured such that said elemental zinc particles contact a skin surface of the human or animal, wherein the plurality of spaced lines are substantially evenly spaced from one other,
- wherein said fabric or substrate forms a plurality of half-cells of an air-zinc battery, for ion exchange with the skin of the human or animal, whereupon the zinc particles in the fabric form a first half cell of a battery circuit, while the body of the human or animal forms a second half cell of the battery circuit with oxygen.

19. The method of claim 18, wherein the oxygen comprises ambient oxygen.

20. The method of claim 18, wherein the oxygen comprises oxygen diffused through the skin.

* * * * *